United States Patent
Kwon

(10) Patent No.: US 8,062,573 B2
(45) Date of Patent: Nov. 22, 2011

(54) SOLID MICRO-PERFORATORS AND METHODS OF USE

(75) Inventor: Sung-Yun Kwon, Fremont, CA (US)

(73) Assignee: TheraJect, Inc., Fremont, CA (US)

( * ) Notice: Subject to any disclaimer, the term of this patent is extended or adjusted under 35 U.S.C. 154(b) by 1955 days.

(21) Appl. No.: 10/528,059

(22) PCT Filed: Sep. 15, 2003

(86) PCT No.: PCT/US03/30881
§ 371 (c)(1),
(2), (4) Date: Mar. 15, 2005

(87) PCT Pub. No.: WO2004/024224
PCT Pub. Date: Mar. 25, 2004

(65) Prior Publication Data
US 2005/0251088 A1 Nov. 10, 2005

Related U.S. Application Data

(60) Provisional application No. 60/411,063, filed on Sep. 16, 2002, provisional application No. 60/441,818, filed on Jan. 21, 2000.

(51) Int. Cl.
*B29C 41/46* (2006.01)
(52) U.S. Cl. ......... 264/319; 604/272; 424/427; 424/428
(58) Field of Classification Search .................. 264/319; 424/427, 428
See application file for complete search history.

(56) References Cited

U.S. PATENT DOCUMENTS

| | | |
|---|---|---|
| 3,596,660 A | 8/1971 | Melone |
| 3,814,097 A | 6/1974 | Ganderton et al. ........... 128/268 |
| 3,964,482 A | 6/1976 | Gerstel et al. |
| 4,109,655 A | 8/1978 | Chacornac |
| 4,592,753 A | 6/1986 | Panoz |
| 4,798,582 A | 1/1989 | Sarath et al. |
| 4,936,835 A | 6/1990 | Haaga |
| 5,250,023 A | 10/1993 | Lee et al. |
| 5,262,128 A | 11/1993 | Leighton et al. |
| 5,279,544 A | 1/1994 | Gross et al. |
| 5,383,512 A | 1/1995 | Jarvis |
| 5,455,611 A | 10/1995 | Simon et al. |
| 5,457,041 A | 10/1995 | Ginaven et al. |
| 5,458,140 A | 10/1995 | Eppstein et al. |
| 5,527,288 A | 6/1996 | Gross et al. |
| 5,591,139 A | 1/1997 | Lin et al. |
| 5,695,484 A | 12/1997 | Cox |
| 5,843,114 A | 12/1998 | Jang |
| 5,848,991 A | 12/1998 | Gross et al. |
| 5,855,211 A | 1/1999 | Nelson |
| 5,855,801 A | 1/1999 | Lin et al. |

(Continued)

FOREIGN PATENT DOCUMENTS

EP 1301238 B1 9/2004

(Continued)

*Primary Examiner* — Christina Johnson
*Assistant Examiner* — Galen Hauth
(74) *Attorney, Agent, or Firm* — Sherr & Vaughn, PLLC

(57) ABSTRACT

Porous microperforators (210A), preferably in an array of multiple perforators are employed for delivery of a drug, where the micro-perforators may dissolve in situ. Suitable micro-perforators may include multiple layers of dissolvable materials to effect sequential drug delivery. In further aspects, contemplated micro-perforators may employ a diagnostic device in which a detector layer or detector is operationally coupled to the micro-perforators.

12 Claims, 5 Drawing Sheets

U.S. PATENT DOCUMENTS

| | | | |
|---|---|---|---|
| 5,879,326 | A | 3/1999 | Godshall et al. |
| 5,928,207 | A | 7/1999 | Pisano et al. |
| 5,983,136 | A | 11/1999 | Kamen |
| 5,990,194 | A | 11/1999 | Dunn et al. |
| 6,013,050 | A | 1/2000 | Bellhouse et al. |
| 6,030,404 | A | 2/2000 | Lawson et al. |
| 6,050,988 | A | 4/2000 | Zuck |
| 6,083,196 | A | 7/2000 | Trautman et al. |
| 6,091,975 | A | 7/2000 | Daddona et al. |
| 6,102,896 | A | 8/2000 | Roser |
| 6,106,751 | A | 8/2000 | Talbot et al. |
| 6,132,755 | A * | 10/2000 | Eicher et al. ............... 424/427 |
| 6,142,939 | A | 11/2000 | Eppstein et al. |
| 6,187,210 | B1 | 2/2001 | Lebouitz et al. |
| 6,219,574 | B1 | 4/2001 | Cormier et al. |
| 6,230,051 | B1 | 5/2001 | Cormier et al. |
| 6,256,533 | B1 | 7/2001 | Yuzhakov et al. |
| 6,312,612 | B1 | 11/2001 | Sherman et al. |
| 6,322,808 | B1 | 11/2001 | Trautman et al. |
| 6,331,266 | B1 | 12/2001 | Powell et al. |
| 6,331,310 | B1 | 12/2001 | Roser et al. |
| 6,334,856 | B1 | 1/2002 | Allen et al. |
| 6,352,506 | B1 | 3/2002 | Eppstein et al. |
| 6,352,722 | B1 | 3/2002 | Blair |
| 6,375,776 | B1 | 4/2002 | Buoni et al. |
| 6,379,324 | B1 | 4/2002 | Garstein et al. |
| 6,406,455 | B1 | 6/2002 | Willis et al. |
| 6,440,096 | B1 | 8/2002 | Lastovich et al. |
| 6,485,453 | B1 | 11/2002 | Buch-Rasmussen et al. |
| 6,611,707 | B1 | 8/2003 | Prausnitz et al. |
| 6,743,211 | B1 | 6/2004 | Prausnitz et al. |
| 2001/0038858 | A1 | 11/2001 | Roser et al. |
| 2001/0053891 | A1 | 12/2001 | Ackley |
| 2002/0006355 | A1 | 1/2002 | Whitson |
| 2002/0009464 | A1 | 1/2002 | Colaco |
| 2002/0012687 | A1 | 1/2002 | Roser et al. |
| 2002/0016562 | A1 | 2/2002 | Cormier et al. |
| 2002/0020688 | A1 | 2/2002 | Sherman et al. |
| 2002/0058067 | A1 | 5/2002 | Blair |
| 2002/0066978 | A1 * | 6/2002 | Kim et al. ............... 264/259 |
| 2002/0082543 | A1 * | 6/2002 | Park et al. ............... 604/21 |
| 2002/0110585 | A1 | 8/2002 | Godbey |
| 2002/0146540 | A1 | 10/2002 | Johnston et al. |
| 2003/0148291 | A1 * | 8/2003 | Robotti ............... 435/6 |
| 2005/0065463 | A1 | 3/2005 | Tobinaga et al. ............... 604/46 |

FOREIGN PATENT DOCUMENTS

| | | |
|---|---|---|
| EP | 1512429 B1 | 9/2005 |
| JP | 2003-238347 | 8/2003 |
| JP | 2003238347 | 8/2003 |

* cited by examiner

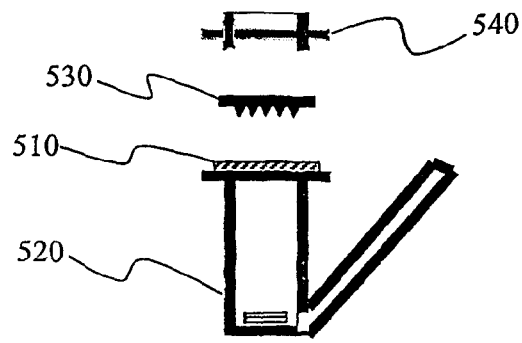
Figure 5A
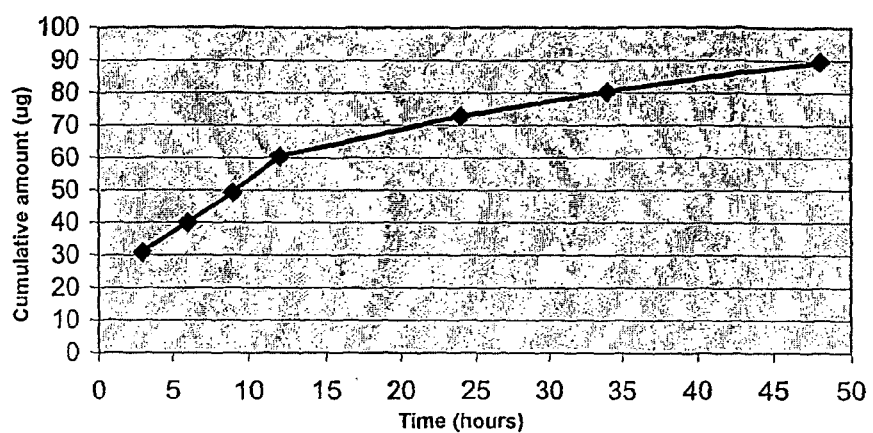
Figure 5B
| Glucose Conc. (mg/dl) | Optical density from bottom chamber | Optical density from top skin |
|---|---|---|
| 0 | 0.22 | 0.24 |
| 100 | 0.75 | 0.9 |
| 200 | 0.95 | 1.01 |
| 300 | 0.77 | 0.85 |
| 500 | 0.94 | 1.15 |
Figure 6

SOLID MICRO-PERFORATORS AND METHODS OF USE

This application is a national stage application of International Application no. PCT/US2003/030881, filed Sep. 15, 2003, which claims the benefit under 35 U.S.C. 119(e)(1) of provisional applications 60/411,063, filed Sep. 16, 2002, and 60/411,818, filed Jan. 21, 2003, and also claims priority under 35 U.S.C. 120 of International Application no. PCT/US03/19820, filed Jun. 19, 2003, all of which are incorporated by reference herein in their entireties.

FIELD OF THE INVENTION

The field of the invention is devices to provide percutaneous access to body fluids, and methods of manufacture therefor, and particularly micro-devices that optionally dissolve upon insertion into the skin.

BACKGROUND OF THE INVENTION

Many new drugs, including vaccines, proteins, peptides and DNA constituents, have been developed for better and more efficient treatment for disease and illness. Especially due to recent advances in molecular biology and biotechnology, increasingly potent pharmaceutical agents, such as recombinant human insulin, growth hormone, follicle stimulating hormone, parathyroid hormone, etanercept, and erythropoietin are available. However, one significant limitation in using these new drugs is often a lack of an efficient drug delivery system, especially where the drug need to be transported across one or more biological barriers at therapeutically effective rates and amounts.

Most drugs are orally administered. However, most protein drugs (e.g., proteins, peptides, and/or nucleic acids, etc.) cannot be effectively adsorbed in this manner due to their degradation in the gastrointestinal tract, poor absorption in intestinal membrane, and/or first pass breakdown by the liver. To circumvent such difficulties, parenteral administration may be employed. Typically such administration relies on injection of the drug into the patient's circulatory system or muscle tissue using standard syringes or catheters. Unfortunately, needle injection often provokes needle phobia, substantial pain, and/or local damage to the skin in many patients. Similarly, withdrawal of body fluids (e.g., whole blood) for diagnostic purposes provokes comparable discomforts. Moreover, and especially where needle injection-based access to body fluids is required for long-term drug administration or long term monitoring of an analyte, numerous challenges arise. For example, needles tend to clog when left over a prolonged period in a patients vascular system. Also, mobility of the patient is generally limited.

Alternatively, transdermal delivery may be employed which usually relies on passive diffusion of a drug across the skin. However, transdermal delivery is often not broadly applicable as the skin presents a relatively effective barrier for numerous drugs (the outermost layer of skin, the stratum corneum, represents a major barrier to drugs with a molecular weight of greater than about 500 Dalton). Once a drug reaches the dermal region (below the epidermal layer), the drug diffuses rapidly to deep tissue layers and other parts of the system via blood circulation. To improve the rate of drug delivery through the skin, chemical enhancers, iontophoresis, electroporation, ultrasound, and heat elements have been used. However, and depending on the particular drug, such techniques frequently fail to provide a therapeutic level of delivery. Worse yet, such techniques will sometimes provoke undesirable skin reactions for long term drug delivery.

Still other known transdermal drug delivery methods include needle-free particle or liquid injection, which are thought reduce incidence of contamination and accidental injuries. However, liquid injection frequently causes pain, and in some cases even sub-dermal hemorrhage. Similarly, exact and consistent ballistic particle injection is typically difficult to achieve and can also cause micro-bleeding in some cases.

Alternatively, micro-needle drug delivery may be employed in which microscopic needles are used that are prepared by micro-fabrication procedures common in the semiconductor industry. Most of such micro-needle devices are designed for drug delivery through a hollow interior of a needle or along an outer surface of a solid needle. However, most of these needles are made from brittle silicon materials, and needle breakage while the needle is inserted in the skin and/or removed from the skin is frequently encountered, especially with inexperienced users. Other micro-needle devices are used as skin perforators which require subsequent patch drug application. However, such administration often results in inconsistent drug dosages, inconvenient usage, and sometimes even in infections.

Therefore, although there are various methods and devices for drug administration known in the art, all or almost all them suffer from one or more disadvantages. Among other things, currently known methods and devices fail to allow controlled administration drugs, to provide prompt initiation and cut-off of drug delivery with improved safety and efficiency, and convenience. Thus, there is still a need for improved methods and devices to overcome the difficulties outlines above.

BRIEF DESCRIPTION OF THE DRAWING

FIG. 5A is a schematic depiction of an experimental setup for determination of ill vitro skin flux.

FIG. 5B is a graph depicting cumulative quantities of a drug transported through the skin of FIG. 5A.

FIG. 6 is a table illustrating in vitro glucose transport through skin using the setup of FIG. 5A in dependence of drug concentration.

SUMMARY OF THE INVENTION

Figure 1:
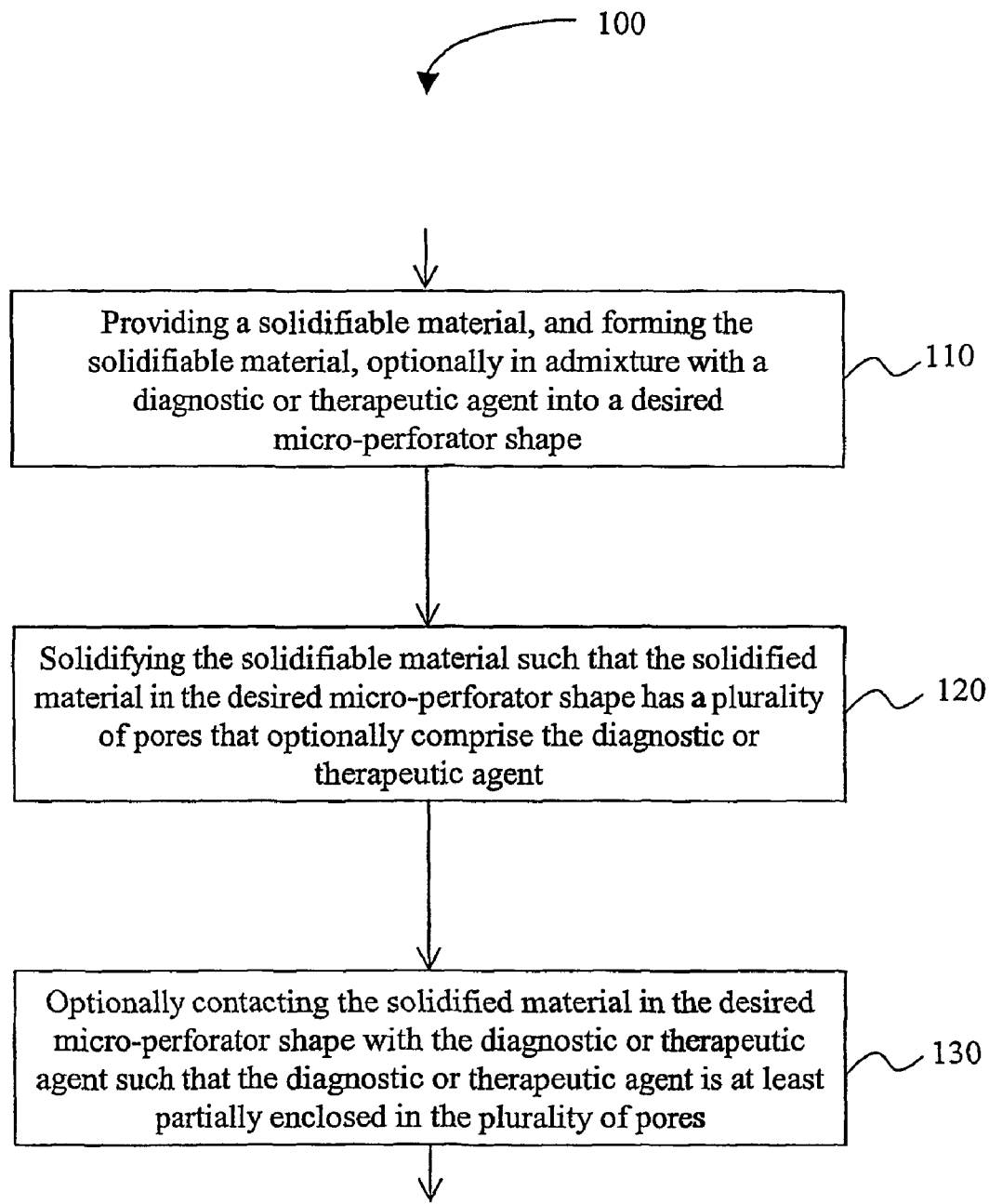
FIG. 1 is a schematic flow chart depicting a method of forming a micro-perforator according to the inventive subject matter.

The present invention is directed to methods and devices in which one or more porous micro-perforators are employed for drug delivery and/or diagnostic purposes. Contemplated micro-perforators are generally solid, may be laminated to include a plurality of drug- or analyte-containing layers, and may optionally dissolve once inserted into a person's skin.

In one aspect of the inventive subject matter, a method of manufacture of a micro-perforator includes one step in which a solidifiable material is provided. The solidifiable material is then formed, optionally in admixture with a diagnostic or therapeutic agent, into a desired micro-perforator shape, wherein the step of forming includes a step of solidifying the solidifiable material such that the solidified material in the desired micro-perforator shape has a plurality of pores that optionally comprise the diagnostic or therapeutic agent. Where the micro-perforator is formed without a diagnostic or therapeutic agent, it is generally preferred that the solidified material in the desired micro-perforator shape is contacted with the diagnostic or therapeutic agent such that the agent is at least partially enclosed in the plurality of pores.

Especially suitable solidifiable materials include sol/gel materials, sinterable materials, and/or a gelling agent or a viscous material, which may include the diagnostic or therapeutic agent. Depending on the particular solidifiable material, porosity in the micro-perforator may be achieved via the conditions chosen during the solidification process (e.g., temperature, alkalinity, etc.). Particularly preferred forming processes include those in which the solidifiable material is applied to a mold, and in which the material is then subjected to pressure (e.g., air or centrifugal) or vacuum to improve settling of the solidifiable material into the mold. In further preferred aspects of such methods, the inventors discovered that the micro-perforator can be shrunk to at least some degree in the mold while drying, and that such shrinkage may be used to decrease the apex angle of the micro-perforators and help to separate from the mold.

Thus, in another aspect of the inventive subject matter, a micro-perforator may comprise a porous material and optionally a diagnostic and/or therapeutic agent, wherein the micro-perforator is substantially insoluble in a skin of a person when applied to the skin Alternatively, however, suitable micro-perforators may also be dissoluble in a skin of a person when applied to the skin over a predetermined period greater than one hour (i.e., slow-dissolving). Especially further contemplated micro-perforators may be fluidly coupled to a pump that delivers a fluid through the micro-perforator into a person's skin (or even below the person's skin).

Further contemplated devices include those in which a plurality of dissolvable micro-perforators are disposed in a predetermined array, wherein at least some of the micro-perforators are coupled to an occlusive backing that enhances dissolution of the micro-perforators. Dissolution in such devices may be enhanced by a fluid from the skin of a person to which the device is coupled, and hydration of skin under occlusive backing film, and wherein at least part of the fluid is retained by the occlusive backing, or by a fluid provided by a fluid reservoir that is fluidly coupled to the micro-perforators (the reservoir is preferably separated from the micro-perforators via an semi-permeable membrane or a rupturable membrane), wherein at least part of the fluid is retained by the occlusive backing.

In a still further aspect of the inventive subject matter, a diagnostic device will comprise a porous micro-perforator that includes at least one of an analyte compartment and a reagent compartment, wherein the at-least one of the analyte compartment and reagent compartment is fluidly coupled to a body fluid of a person when the micro-perforator is inserted into a skin of the person, and wherein the at least one of the analyte compartment and reagent compartment is operationally coupled to a detector.

Various objects, features, aspects and advantages of the present invention will become more apparent from the following detailed description of preferred embodiments of the invention.

DETAILED DESCRIPTION

The inventors discovered that one or more micro-perforators can be employed in a drug delivery system and/or in various diagnostic devices, wherein such systems and devices are preferably topically applied to the skin or other body surface, including mucous membranes, and cornea.

In especially preferred aspects, contemplated systems and devices include an array of one or more porous micro-perforators that may have various shapes and sizes, wherein at least some of the micro-perforators include a drug or reagent that is distributed throughout rather the micro-perforator. Alternatively, and especially where a micro-perforator dissolves relatively rapidly, no drug or other reagent may be included and the micro-perforator may then be employed to form a reagent channel in the skin. The term "porous" as used herein refers to a plurality of voids, which may or may not form a fluidly continuous network of voids. Thus, a porous micro-perforator may retain at least partially enclosed fluid within a plurality of pores, but also transport a fluid through a network of pores that are fluidly coupled to each other.

In some aspects of the inventive subject matter, the porous micro-perforator is prepared such that the perforator will not dissolve or undergo biodegradation in a relatively short time (i.e., at least 95% of the micro-perforator remain solid and after one hour) but releases a selected drug from or through the pores. In other aspects, the porous micro-perforator is prepared such that the perforator will dissolve or undergo biodegradation over a predetermined period (e.g., at least 50% of the micro-perforator dissolves after one hour) while releasing a selected drug from or through the pores, or thereby creating a conduit for a reagent or therapeutic drug.

Particularly preferred devices will include multiple micro-perforators and may further include a reservoir with a second drug (e.g., contained in a patch and fluidly coupled to the micro-perforator array containing either the same or different drug). It should be particularly appreciated that by creating a drug transport channel or conduit in the skin (and especially in the outermost layer), various advantages can be achieved. Among other things, the barrier properties of skin can be diminished, drug delivery rate can be controlled, and access can be provided to body fluids that are to be monitored. Optionally, contemplated devices may be formed as a dermal patch that includes a ring of adhesive that bonds with and holds the reservoir against a person's skin. Where a drug or other reagent reservoir is included, such reservoirs may be separately opened to deliver the drug or other reagent through the skin channels formed by such devices.

Alternatively, contemplated micro-perforators may also be employed in a diagnostic device which may provide a test result in visually discernible form (e.g., formation of color) or electronic form (e.g., electric potential or current). For example, a needle assembly maybe formed that includes at least one micro-perforator for penetrating a stratum corneum of a patient, a reservoir connected to the micro-perforator assembly for delivery of a selected chemical to the micro-perforator(s), and one or more micro-perforators connected to a signal processing apparatus (which may be part of a patch or may be an external device). Micro-perforators are preferably made from the same material as the micro-perforators, but may also be different. Typically contemplated micro-perforators will be adjacent to at least one micro-perforator and sense a selected local chemical or physical attribute in the patient (e.g., at selected times relative to delivery of a drug or reagent). For example, a micro-perforator can incorporate a sensor gel, such as a glucose oxidase gel that undergoes a change in color or free electron concentration or some other attribute in the presence of glucose.

Suitable porous micro-perforators may be fabricated from various materials. However, it is generally preferred that the material is a solidifiable material that conforms in the unsolidified form to a mold (e.g., by gravity, or using positive and/or negative pressure), and that is then solidified in the mold by drying, heating, compression, or other process to yield a porous micro-perforator. Thus, preferred materials include sol/gel materials, sinterable materials, gelling agents, viscous materials, and powered solid materials, and it should be especially recognized that by the choice of the materials and production conditions pore size can be controlled. Additionally, and at least in some aspects, formation of the micro-perforator may take place under conditions that preserve bioactivity of the drug that is to be delivered via the micro-perforator. For example, where the drug is a heat labile peptide or a protein, a sol/gel process may be employed at room temperature and ambient pressure.

Further advantages of using preferred materials above include control over (a) pore size, which renders such transcutaneous independent of the drug molecular weight, (b) penetration depth for injection or for intrusion, and (c) drug release profile. Furthermore, preferred materials will improve self-use by fabrication of micro-perforators into patch-like devices, reduce toxicity and improve biocompatibility, and permit relatively easy immobilization of enzymes on the material surface.

Where it is desirable that relatively large quantities of a drug or reagent are delivered through the micro-perforators, it is generally preferred that a reservoir (optionally coupled to a pump) is fluidly coupled to the micro-perforators. Furthermore, where dissolvable micro-perforators are used, a patch with liquid reservoir is configured to release the liquid into a micro-perforator array when the patch is applied to the skin. The released liquid helps dissolve, and thereby deliver, a chemical in the micro-perforators. Alternatively, a pump (providing negative pressure) may also be used to collect metabolites or other compounds of interest.

Further contemplated configurations, compositions, and methods of fabrication and use are provided in the sections below and will provide further exemplary embodiments of the inventive concept presented herein.

Contemplated Micro-Perforators

Contemplated micro-perforators and micro-perforator based systems are particularly advantageous when applied to the surface of the skin of a person (mammal, or other non-mammalian animal) as the skin presents a significant obstacle for most topically applied drugs as well as a barrier against loss of body fluids from the organism. A normal human skin typically includes a stratum corneum as a top layer, followed by an epidermal layer (or epidermis), which is in turn followed by a dermal layer (or dermis). The stratum corneum (thickness of about 10 and 20 micrometers) is predominantly formed from dead cells that are surrounded by a hydrophobic extra-cellular matrix of lipids, mainly ceramide. Because of this structural and compositional uniqueness, the stratum corneum typically presents the greatest barrier to transdermal flux of drugs, chemicals or other molecules into the body, and transdermal efflux of body fluids and other analytes. The stratum corneum is continuously renewed by shedding of corneum cells, with an average turnover time of 2-3 weeks. Below the stratum corneum is the viable epidermis or epidermal layer, with a thickness of typically between 50 and 100 micrometers. It should be noted that in most instances the epidermis contains no blood vessels and freely exchanges metabolites by diffusion to and from the dermis, located immediately below the epidermis. The dermis is between 1 and 3 mm thick and contains blood vessels, lymphatic tissue, and nerves. Once a drug or other chemical reaches the dermal layer, the drug will readily enter the circulatory system. A dense collection of potent antigen-presenting cells, including Langerhans cells, cover about 25 percent of the epidermal/dermal boundary (It should be especially appreciated that a vaccine that penetrates the stratum corneum is typically taken up by Langerhans cells, which migrate to lymph nodes and activate an antigen-specific immune reaction). Moreover, there is a relatively strong correlation between the chemical composition of the interstitial fluid in epidermal layer and blood (it is generally accepted that glucose in interstitial fluid is indicator of glucose in blood), which allows to develop a pain-free and blood free diagnostic test system.

Based on these and other considerations, a micro-perforator-based drug/vaccine delivery system or a micro-perforator based diagnostic system will preferably include an array of one or more micro-perforators, preferably between 1-200 in an area of about 10 cm$^2$, wherein at least a portion of the micro-perforators is either pointed or otherwise sharpened for perforation or penetration of the skin. In further particularly preferred aspects, each micro-perforator is sufficiently strong to pierce the stratum corneum.

While in some instances it is preferred that the micro-perforator will substantially not dissolve, melt, or be degraded over a predetermined period (e.g., at least 95% will remain undissolved or undegraded for at least 6 hours) after the micro-perforator and drug have penetrated into the skin, it should also be appreciated that relatively fast dissolving micro-perforators are also specifically contemplated. With respect to the particular shape, it should be recognized that all shapes are suitable so long as the micro-perforator will be able to at least partially penetrate the skin, and particularly the stratum corneum. Therefore, suitable shapes include cones with a cusp-like point that may provide extra penetration power, or cones with a conventional linear penetration point. Further contemplated shapes include cylinder-plus-cone shapes for a circular cylinder and for a rectangular (or, more generally, polygonal) cylinder, respectively. Additionally, micro-perforators may be configured as a slicing blade (straight or serrated) that contact and penetrate the skin. Other shapes with a pointed or blade end are also contemplated suitable for use herein, and may additionally or optionally include straight or tapered shafts, or include pyramids or wedges or blades. Optionally in order to improve the penetration, inserting speed of microneedle patch can be adjusted with a device (see our copending application Ser. No. 10/179, 749 which is incorporated by reference herein).

While not limiting to the inventive subject matter, it is generally preferred that the outer diameter of a micro-perforator is greatest at the base (i.e. portion distal to the skin when the micro-perforator is inserted), and will have a diameter of between about 10-1000 μm, while the diameter near the front end (i.e. portion proximal to the skin when the micro-perforator is inserted) is preferably between about 1-100 μm. The length of a micro-perforator is typically in a range of between about 1-2000 μm, and more preferably in a range 100-1000 μm. Furthermore, suitable aspect ratios may vary considerably, however, particularly preferred micro-perforators have an aspect ratio (length divided by diameter) of at least 1.

With respect to the particular dimensions of contemplated micro-perforators, it should be recognized that the length, and diameters, and general shape may vary depending on the particular location employed. The skin is not a smooth and rugged surface and has different depths microscopically. In addition, the thickness of the stratum corneum and elasticity of the skin varies from person to person and from location to location on any given person's body. A desirable penetration depth will therefore have a range, rather than a single value, for effective drug delivery and for relatively painless and bloodless penetration. Penetration depth of a micro-perforator can affect pain as well as delivery efficiency. Consequently, in transdermal applications, the penetrated depth of the micro-perforator is preferably less than 100 μm so that a perforator, inserted into the skin through the stratum corneum, does not penetrate past the epidermis. Such depth is considered particularly advantageous when contact with nerves and blood vessels is to be minimized and/or avoided. Nevertheless, the actual length of the micro-perforators can be greater than the thickness of the stratum corneum as the micro-perforator may not be fully inserted into the skin (e.g., because of elasticity and/or rough surface of the skin).

In other examples, penetration of the micro-perforator to the dermis and even lower may be required (e.g., for drug delivery to the circulatory system). Of course, it should be recognized that the penetrating portion of a micro-perforator can be optimized to a desired application by adjusting selected variables, including micro-perforator length, dimension, mechanical properties of the micro-perforator, inserting speed, or micro-perforator-based system, and by accounting for specific skin elasticity, skin hardness and surface roughness.

Suitable micro-perforators may include air, medical gases, therapeutic agents, and/or diagnostic reagents disposed within at least some of the pores or pore network, and it should be appreciated that all types of such included agents are deemed suitable herein. Inclusion of the agents may be performed by soaking the perforator in a suitable solution or formulation of the agent, but may also be performed as part of the manufacture process (see below). Contemplated medical gases include NO, $O_2$, $CO_2$, etc., while suitable therapeutic agents include small molecule drugs (antiviral drugs, antibacterial drugs, anti-inflammatory drugs, analgesic drugs, metabolically active drugs, psychoactive drugs, etc.), bio-molecule drugs (e.g., nucleic acid-type drugs, coding sequences, antisense sequences, interfering sequences, polypeptide drugs, antibodies, cytokines, etc.), vitamins, nutritional supplements, contraceptives, etc. Similarly, the specific nature of diagnostic reagents is not limited, and suitable diagnostic reagents include enzymes, chromogenic, fluorogenic, luminogenic substrates, co-substrates, etc.

Where appropriate, contemplated micro-perforators may be coated with desirable agents that will facilitate penetration through the skin, prevent inflammation and/or infection, reduce perceived pain, and/or other compounds/compositions that aid in a specific therapeutic and/or diagnostic function. Especially preferred micro-perforators will include laminated micro-perforators in which a micro-perforator has a plurality of optionally porous layers, wherein at least one of the layers will dissolve over time (e.g., 30 minutes after insertion into the skin). Such laminated micro-perforators may advantageously provide multiple doses of one or more drug (e.g., first drug in the outermost layer, second drug in the layer below the outermost layer, etc.), and may further be employed where subsequent dosages of the same or different drug are applied (e.g., first drug in the outermost layer, no drug in the layer below the outermost layer, followed by first drug in the layer below the drug-less layer, etc.).

Figure 2A:
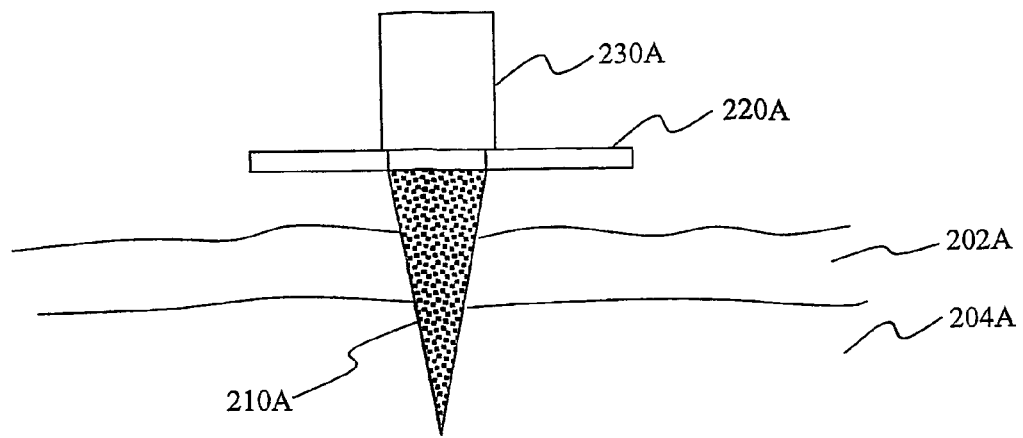
FIG. 2A is a schematic exemplary illustration of a non-dissolvable micro-perforator according to the inventive subject matter.
Figure 2B:
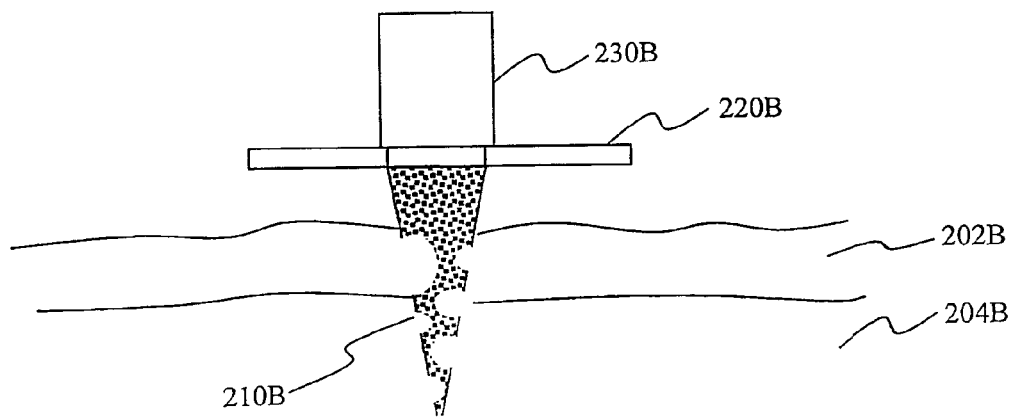
FIG. 2B is a schematic exemplary illustration of a dissolvable micro-perforator according to the inventive subject matter.

Thus, one exemplary insoluble micro-perforator may have a configuration as depicted in FIG. 2A in which a porous micro-perforator 210A is inserted into the skin having a stratum corneum layer 202A and a dermis layer 204A. Disposed within the pores is diagnostic and/or therapeutic agent (filled circles) that is released from the perforator over a predetermined period. The porous micro-perforator 210A is further coupled to a liquid and/or gas permeable base layer 220A, which may optionally be fluidly coupled to a pump 230A. Alternatively, a micro-perforator may be dissoluble in the skin as illustrated in FIG. 2B. Here, the micro-perforator 210B is inserted into the skin having a stratum corneum layer 202B and a dermis layer 204B. Disposed within the pores is diagnostic and/or therapeutic agent (filled circles) that is released from the perforator over a predetermined period. The porous micro-perforator 210B is further coupled to a liquid and/or gas permeable base layer 220B, which may optionally be fluidly coupled to a pump 230B.

Contemplated Systems Comprising Micro-Perforators

In further preferred aspects, one or more micro-perforators are coupled to one or more layers that provide mechanical stability and/or a fluid or gas (e.g. reagent or drug, same of different that those in the pores of the perforator) to form a therapeutic and/or analytic device (also referred to herein as micro-perforator device, or MPD). Such devices may consequently be employed for immediate or continuous drug delivery, or for immediate or continuous analysis for the presence and/or quantity of a specific analyte.

Therefore, in one aspect of the inventive subject matter, a function of an MPD is to pierce the stratum corneum, to provide prompt initiation and cut-off (e.g., by perforator removal or immediate perforator dissolution) of drug delivery, and/or to help form and maintain a channel for drug delivery or body fluid monitoring. Thus, any biocompatible material that is sufficiently solid and porous can serve as a micro-perforator, but ceramic-like materials are preferred in contemplated MPDs (mainly due to relative inertness, biocompatibility, and mechanical strength).

Figure 3A:
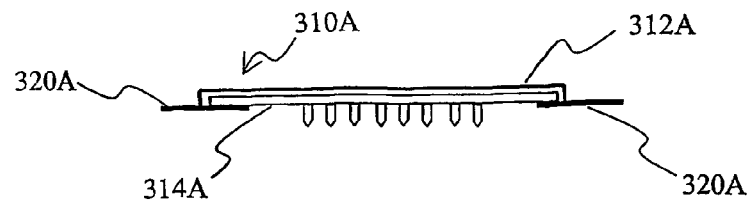
FIG. 3A is a schematic exemplary illustration of a device comprising a plurality of dissolvable micro-perforators according to the inventive subject matter.

One exemplary MPD as depicted in FIG. 3A may therefore include a basal layer 310A comprising a backing 312A and an array of one or more micro-perforators 314A. An adhesive strip 320A is optionally coupled to the basal layer and/or array to retain the MPD in place. Active ingredients (e.g., a drug or drug solid solution) are at least partially enclosed in the pores of the perforator, and the basal layer is relatively thin (e.g. between less than one mm to several mm) and is preferably impermeable for fluids (occlusive layer). Such configurations are thought to be advantageous for administration of small doses of a relatively potent or concentrated drug, or for immediate drug delivery. Alternatively, an MPD may comprise an array of micro-perforators and a porous basal layer that optionally serves as a drug or reagent reservoir. Active ingredients may be contained in the perforator and/or in the basal layer. In such configurations, the basal layer will typically have a different chemical composition from the MPD's outermost layer, which will be in most cases a fluid impermeable backing layer.

Figure 3B:
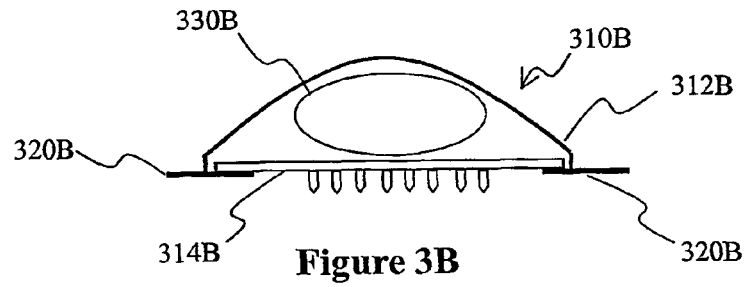
FIG. 3B is a schematic exemplary illustration of the device of FIG. 3A additionally comprising a fluid reservoir.

A more complex configuration of contemplated MPDs includes a patch in which the drug or reagent is contained in the micro-perforators and in a reservoir as depicted in FIG. 3B. Here, a portion of the basal layer 310B will contain a drug reservoir 330B. The array 314B, the backing 312B, and the adhesive 320B are depicted similarly as above. In such configurations, a first set of micro-perforators is oriented to penetrate the stratum corneum of the skin, and a second set of micro-perforators is oppositely oriented to penetrate a membrane that surrounds or contains fluid in the reservoir patch (not shown). Alternatively, the reservoir can be separately applied after MPD application, or can be combined with the MPD layers into an integrated MPD. It should be appreciated that the reservoir can have a variety of compositions or formulations depending on targeted drug release profile. Such configurations are deemed particularly suitable for relatively large doses and/or complex delivery. In yet further contemplated aspects, an MPD will comprise empty micro-perforators while the drug or diagnostic reagent is contained in a basal layer and/or reservoir only. Depending on the drug solubility and concentration, drug release from the basal layer can be controlled. Furthermore, where porous ceramic materials are employed for an MPD, and where no drug is included in the micro-perforators, skin conduits can be formed for a predetermined period for subsequent drug delivery or diagnostic applications. Therefore, a basal layer will provide at least in some embodiments protection to isolate a perforated skin region from contamination (the basal layer or a peripheral adhesive may further contain anti-bacterial agents), while in other embodiments the basal layer will create occlusion to hydrate perforated skin to enhance flux of fluids.

Thus, one function of a basal layer in an MPD with reservoir is to isolate the drug reservoir until the patch substance is injected and to serve as a transport bridge between the reservoir and the remainder of the system. The basal layer material can be same as the solid matrix material, or may be a different material, depending on the application. In an MPD without reservoir, the basal layer can be laminated with one or more additional layers or materials for controlled release. The outermost basal layer can act as an impermeable backing film to protect against any virus or bacterium that might otherwise invade the skin perforation region. In order to avoid back diffusion from other parts of the MPD, this layer should have low drug solubility. Where additional and sustained drug release is required, the basal layer can be constructed to contain more of a drug or to provide a conduit to a secondary reservoir. It is useful to have anti-virus and/or anti-bacterial protection in the basal layer to suppress infection. In order to vary or control the drug delivery rate, an external physical enhancement system, using iontophoresis, or sonophoresis, piezoelectric response or a similar response, can be provided as part of a basal layer and/or an overlay layer.

An exemplary preferred patch may thus include a drug reservoir, containing a drug that may be the same as or different from the drug contained in the micro-perforator, wherein the reservoir is located proximal to the micro-perforator array. The patch preferably includes a backing film that surrounds the drug reservoir and further includes an annular adhesive region that surrounds and seals off the skin perforation region. An optional plastic release liner is peeled off before skin penetration which protects the MPD system until the liner is peeled off.

Particularly preferred MPD patches include a reservoir containing a liquid or gel form of a drug and one or more micro-perforators extending from at least a part of the reservoir's surface. The micro-perforators associated with the patch system penetrate the stratum corneum of the skin to enhance percutaneous drug administration and to provide prompt drug delivery and/or prompt drug cut off. In the MPD patch, the micro-perforators and the reservoir can be constructed as a single unit or as separate units. The patch reservoir is intended to provide sustained, controllable delivery of a liquid or semi-liquid (second) drug into or across a biological barrier so that diffusion channels are created and remain open after insertion of a micro-perforator (solid matrix plus drug). The size, shape, composition and density of micro-perforators, as well as the aqueous solution formulation, affect the drug release rate through the skin channels. Alternatively, other control mechanisms such as iontophoresis, sonophoresis, heating components and mechanical vibration forces can accelerate, decelerate or otherwise control drug transport through the stratum corneum. In a preferred embodiment, drug molecules in a reservoir in the MPD patch flow through the channel in the stratum corneum created by MPD and into the epidermis or dermis, depending upon the application.

A MPD can transport therapeutic and/or prophylactic agents, including drugs and vaccine and other bio-active molecules, across skin and other tissues, and permits drug delivery and access to body fluids across skin or other tissue barriers, with minimal damage, pain and/or irritation at the tissue. In drug delivery applications, a micro-perforator optionally is primarily composed of an active drug and a non-dissolving, continuously porous, solid matrix depending on a desired drug profile. The MPD will therefore act as an immediate drug source and as a channel creator for subsequent drug delivery through skin. In a diagnostic application, a body fluid (e.g., interstitial fluid or blood) will pass through the pores to a sensor layer of the MPD system, optionally connected to a vacuum pump. Depending on the application, an osmotically active or anti-irritant compound can have a beneficial effect. In some diagnostic applications a MPD can include or consist of micro-perforators, using an immobilizing enzyme inside the pores of porous materials (see below). For example, glucoseoxidase can be immobilized on a ceramic needle and can be used for glucose monitoring.

In a further contemplated aspect of the inventive subject matter, the MPD includes a piezoelectric ceramic material that responds to a voltage difference between two spaced apart locations on the ceramic material. Application of an alternating potential between such locations on the ceramic micro-perforator will cause the micro-perforator volume and pore volumes to change periodically, through vibrations. As a result, the immobilized solution in the pores will be released at a controllably variable rate after the micro-perforator has penetrated to the desired layer. Similarly, localized vibration of piezoelectric materials can enhance drug diffusion.

Alternatively, one or more porous micro-perforators are connected to a pump that applies positive pressure to deliver a liquid containing a selected drug or chemical at a selected delivery rate from a source to and through the micro-perforator material. Optionally, or additionally, the pump may be configured to apply negative pressure (e.g., a mild vacuum) to draw liquid into and through the porous micro-perforator material and to a detector or electrode for quantitative and/or qualitative analysis monitoring. For example, generation of antibodies or other blood compounds may be monitored at one or more times after delivery of a drug at a selected drug profile rate to a patient.

Thus, the inventors also contemplate a diagnostic device that comprises an array of micro-perforators in which at least one micro-perforator sensor or other sensor is integrated with the micro-perforator(s). Preferably, at least one micro-perforator is adjacent to at least one micro-perforator sensor, and all micro-perforators and micro-perforator sensors are configured to penetrate a stratum corneum. In some preferred aspects, a micro-perforator delivers a selected chemical from a reservoir through the stratum corneum to the skin, while an adjacent micro-perforator sensor senses or measures at least one analyte (e.g., pH, $PO_2$, $pCO_2$, water-to-alkoxide ratio, temperature, electrolyte concentration, metabolite concentration, chemical composition) and/or at least one local physical attribute (e.g., light absorption in a selected wavelength range or a bio-electrical parameter) at one or more of a selected time points to monitor the effects of introduction of the selected chemical through the micro-perforator. Alternatively, two micro-perforator sensors are spaced apart and act cooperatively to sense or measure transport (e.g., diffusion) of, or a local chemical and/or physical attribute associated with delivery of, the selected chemical.

In still further contemplated aspects, one or more micro-perforators will provide a conduit for an analyte in the skin, wherein the analyte will actively (e.g., via pump) or passively (e.g., via adsorbent backing layer or concentration gradient) move from the skin into and out of the micro-perforator to contact a detector that is fluidly coupled to the micro-perforator. Suitable detectors will include those that provide a visually detectable signal (e.g., a layer in which a chromogenic reaction takes place), or an electronically or optically detectable signal (e.g., luminogenic, fluorogenic signal, or change in electric potential via an oxidoreductase). The so generated signal can then be visually detected, or transferred to an analyzer that identifies presence and/or amount of a specific analyte.

Alternatively, one or more micro-perforators will contact the analyte in the skin, wherein the analyte may react with a reagent in the micro-perforator to provide a detectable event (e.g., calorimetrically or luminometrically detectable event, electronically detectable event) in the micro-perforator, which is detected by the detector (e.g. photocell, voltametric/amperometric detector) that is coupled to the micro-perforator. Once more, where desirable, the so generated signal can then be visually detected, or transferred to an analyzer that identifies presence and/or amount of a specific analyte.

Figure 4:
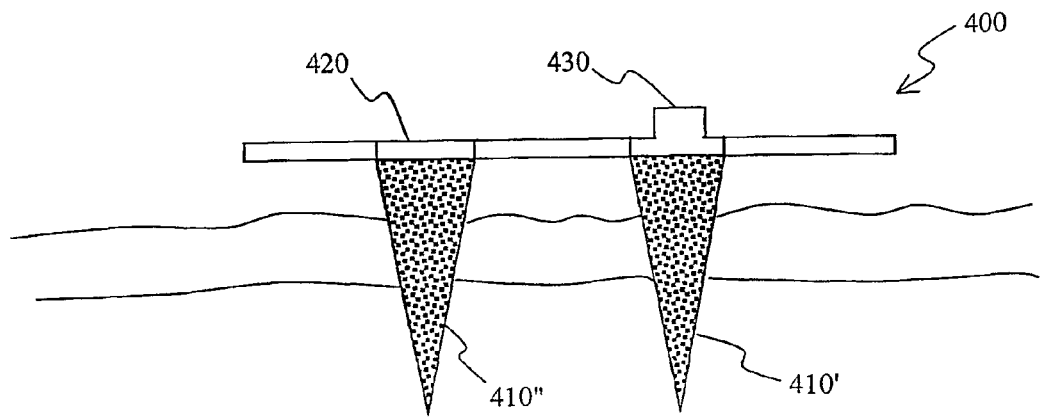
FIG. 4 is a schematic exemplary illustration of a diagnostic device comprising micro-perforators according to the inventive subject matter.

An exemplary diagnostic device is depicted in FIG. 4, in which device 400 has a first and a second micro-perforator 410' and 410", respectively. Each of the micro-perforators 410' and 410" include a plurality of voids that form an analyte and/or reagent compartment (dots in perforators), that is in fluid communication with interstitial fluid (not shown). Detection of the analyte in the interstitial fluid can be done directly on the device 400 via a detection layer 420 that is fluidly coupled to the micro-perforator 410' and that provides a visually identifiable signal (e.g., color formation of a chromogenic reagent), or indirectly via an electronic sensor 430 (e.g., photocell, voltametric/amperometric detector) that is functionally coupled to the micro-perforator. Alternatively, the perforator(s) may also dissolve to create a channel through which an analyte is transported from the interstitial fluid to the detector, detector layer, or intermediary carrier from which the analyte is then detected (see e.g., examples below).

Contemplated Methods of Manufacture of Micro-perforators and Systems

It is generally contemplated that micro-perforators may be fabricated using numerous manners of manufacture, and all processes leading to such perforators are deemed suitable for use herein (e.g., micro-machining, etching, photolithographic processes, etc.). However, it is generally preferred as exemplarily depicted in method 100 of FIG. 1, that contemplated micro-perforators are formed in a step 110 from a solidifiable material into a desired micro-perforator shape, optionally in admixture with a diagnostic or therapeutic agent.

In especially preferred aspects, forming the solidifiable material further includes a step 120 of solidifying the solidifiable material in a manner such that the solidified material (once it is in the desired micro-perforator shape) has a plurality of pores that optionally comprise the diagnostic or therapeutic agent. Where the micro-perforators are fabricated in the absence of the diagnostic or therapeutic agent, it is contemplated that the solidified micro-perforators may be contacted (e.g., soaked, incubated, etc.) with the diagnostic or therapeutic agent such that the diagnostic or therapeutic agent is at least partially enclosed in the plurality of pores as depicted in step 130 of method 100.

For example, forming the solidifiable material may include a sol-gel process, in which a drug-containing solvent/solute slurry is prepared and molded into a desired micro-perforator shape using a micro mold. Pressure, preferably by centrifuge, is applied to fill the slurry to the end of micro mold. The so prepared molded slurry is then dried at a selected, relatively low temperature to yield the micro-perforator structure that contains the aqueous drug solution in one or more of its pores. In this process, pH, alkaline concentration and/or other relevant parameters are controlled to provide a desired properties, including porosity for a controlled flow of the drug or other chemical into or through the epidermal layer or dermal layer of a patient's body.

In a typical contemplated sol-gel process of ceramic materials, acid and base addition is used to control porosity of the resulting material. For example, strong acid (pH of about 2) promotes formation of small pore size material (after drying) with relatively slow drug release. On the other hand, a neutral environment (pH about 4-9) promotes formation of lower density, high pore size material with relatively faster drug release. It should be especially appreciated that sol-gel fabrication is typically a low temperature, inorganic polymerization process that helps preserve the bioactivity of the drug constituents.

In an exemplary sol-gel process, a selected ceramic (e.g., silica) and a selected solvent (e.g., methanol) are mixed with a selected aqueous drug or chemical solution at a temperature in a temperature range of between about 40-300° C. (preferably about 60° C.). Micro-perforator porosity is adjusted by varying the water-to-alkoxide ratio, pH and/or alkoxide concentration, as well as the aging and drying conditions.

In such compositions, the porosity (void fraction of the micro-perforator) can be between 10-80 percent, although the preferred range for some drug delivery applications may be in the range 10-40 percent. Because of this relatively high porosity, a ceramic needle can be provided with an immobilized enzyme on a ceramic surface and/or within some or all of the pores. For example, a lipase can be immobilized in silica pre-polymer from tetramethoxysilane, methyltrimethoxysilane with an acidic catalyst and polyhydrogensiloxanes with variable content of silanol groups. In some instances, an immobilized enzyme is more stable and maintains its bioactivity longer than does the enzyme in solution.

In a further step, the mixture is molded into one or more micro-perforators of desired shape, which are then aged, allowed to solidify, and dried at room temperature for approximately 6 hours to two days. The micro-perforators are then assembled into an appropriate array as a MPD for subsequent use. Other suitable ceramic-solvent combinations include MgO and methanol, $Al_2O_3$ and methanol, or hydroxyapatite and ethanol. Still further alternative materials include modified silicates (e.g., tetramethyloithosilicate ("TMOS")), organically modified alkoxide (e.g., methyltrimethoxysilane ("MIMS"), or vinyltrimethoxysilane ("VTMS")). Particular preferred examples of starting materials include hydroxyapatite, calcium phosphate ($CaPO_x$), tricalcium phosphate ($Ca_3PO_y$), titanium oxide ($TiO_2$), barium titanate ($BaTiO_3$), calcium aluminate ($CaOAl_2O_3$), aluminum oxide ($Al_2O_2$), glass-ceramics, other ceramic materials and substantially pure carbon. In some instances, the drying phase of a sol-gel process may rely partly or wholly on freeze drying of aqueous sols or powder suspensions. Nucleation and growth of solid crystals, as part of the drying process, may be used to control size, shape and/or local distribution of pores resulting from elimination of the solvent. This drying step can proceed with or without re-melting of the solid.

Alternatively, micro-perforators may be fabricated using sintering of suitable sinterable materials. For example, where the sinterable material is or comprises a ceramic powder (e.g., $TiO_2$), controlled conditions may be applied to yield a desired porosity and pore size. Of course, it should be appreciated that alternative sinterable materials, including various metals, polymers, composite powders, and all reasonable mixtures thereof may be employed to substitute ceramics or to be combined with ceramic material. Suitable metals and alloys for micro-perforator fabrication include stainless steel, cobalt-chromium alloys, titanium alloys, nickel, tantalum, molybdenum, tungsten, platinum, gold and silver. Suitable polymers for micro-perforator fabrication include polyolefins, polyamides, acrylic polymers and fluorocarbon polymers. The so formed micro-perforator is then filled with the therapeutic drug, analyte, or other reagent by capillary action. It should be recognized that in both methods of manufacture (sol/gel and sinter process), the preferably aqueous drug solution is released from the micro-perforator pores at a predictable rate after insertion of an array of one or more of the micro-perforators into the skin.

A typical sintering process may therefore include a step in which a selected ceramic powder is molded in a mold into micro-perforators. The powder is then compressed and sintered at a predetermined temperature and pressure, which is adjusted to provide a desired porosity and pore size for the sintered material. The sintered and cooled micro-perforators are then immersed in a selected aqueous drug or chemical solution for a predetermined time (preferably at least one minute) to allow the aqueous solution to be taken up into the pores of the sintered material. If the solution is provided under elevated pressure, the immersion time may be reduced. In yet another step, one or more micro-perforators are assembled into a patch or other configuration for subsequent use.

In yet another embodiment, a mixture of a selected gelling agent and a selected liquid is deposited to substantially fill a micro-perforator mold having at least one mold wall. A portion of the liquid escapes from the mixture (e.g., by evaporation and/or diffusion) during the drying process, thereby causing the mixture in the mold to shrink in volume and to become displaced from at least one mold wall, where the amount of shrinkage is controlled by the nature and amount of the gelling agent. There are numerous gelling agents known in the art (hydroxymethyl cellulose, hydroxypropyl guar, amorphous silica, etc.), and all of these are considered suitable for use herein. This shrinkage can produce a sharpening of the needle tip angle, for example from 35° to a smaller number, such as 25-30°. An additional advantage of such fabrication method is that the micro-perforator can be fabricated at room temperature and pressure so that any protein drug present is not degraded by use of high temperatures.

In a still further contemplated aspect of manufacture of micro-perforators, a selected viscous material, possibly including a gas entrapped in the viscous material, is deposited in a microporous mold having at least one mold wall or mold wall section that allows passage of the entrapped gas through the mold wall (e.g., comprising a micro-dialysis membrane with molecular cutoff lower than viscous material). A positive force (e.g., air pressure, centrifugal force) is applied to the viscous material in the mold to cause at least a portion of the entrapped gas to move through the mold wall and to thereby become removed from the viscous material. Alternatively, a vacuum may be applied to an exposed surface of the micro-perforator, and one or more gas bubbles are drawn out of the micro-perforator material and into or through the vacuum device.

Alternatively, a solid material (e.g., drug powder or gelling agent powder) is pre-packed into a micro-mold to form a dry matrix. A selected gel or liquid is then is added and external force is applied to the pre-packed mold. Optionally, the dried matrix has a particular-surface concentration or morphology that facilitates penetration of a patient's stratum corneum. By adding sugar or humectants in the gel matrix, the dissolution rate of the micro-perforators, through exposure to body fluids, can be controlled (e.g. increased or decreased).

It should be especially recognized that all of the above methods of manufacture could be repeatedly performed using micro-molds of increasing size to obtain a laminated micro-perforator. Such laminated micro-perforators may advantageously include two or more layers porous layers that dissolve at a predetermined rate to allow sequential release of multiple drugs/analytes (which may or may not the same. Similarly, intermittent release may be achieved by alternating drug-containing layers with non-drug-containing layers.

Preparation of a MPD will typically include a step in which one or more of previously prepared micro-perforators are assembled onto a-carrier film or platform. Such assembly may be manual, or automated, or may be performed by casting a layer over a mold that includes previously formed micro-perforators. Depending on the particular-application, the layer to which the micro-perforators are coupled to is permeable for a liquid, or impermeable. Where a permeable layer is employed, it is especially contemplated that such layer is fluidly coupled to a reservoir, and further optionally a pump. Alternatively, micro-perforators may also be coupled to a diagnostic device that provides a visually discernible readout, or an electronically detectable signal.

EXAMPLES

The following protocols are provided as exemplary guidance for fabrication of suitable micro-perforators and devices therefor.

Sol-gel Process

Silicate with methanol is mixed with a drug in aqueous solution at 60° C. The so formed gel is molded (e.g., by injection molding, compression molding, or embossing) in a suitable mold for shaping micro-perforators in a desirable shape. The formed material is then aged and solidified. After aging, the gel is dried at 60-10020 C. Porosity in such a process can be adjusted by varying water-to-alkoxide ratio, pH, alkoxide concentration, aging (syneresis) and drying condition. Non-dissolving and biocompatible ceramic needles can be used in delivering drug and sampling body fluid for diagnostic application.

Powder Sintering

Sinterable particle like ceramic material is filled into a mold. The temperature and/or pressure is increased up to sintering process start. Once the sintering reaction is complete, the material is cooled down to room temperature and the micro-perforator is separated from the mold. The porous micro-perforator is then incubated in a solution that includes the therapeutic/diagnostic agent, and assembled to patch.

Gel/Sol and Sinter Materials

Silica, Tetramethylorthosilicate (TMOS), organically modified alkoxide, including methyltrimethoxysilane (MTMS), vinyltrimethoxysilane (VTMS). Hydroxyapatite, Calcium phospate, Tricalciumphospate [$Ca_3(PO_4)_2$], Titanium Oxide ($TiO_2$), Barium Titanate ($BaTiO_3$), Calcium aluminate ($CaOAl_2O_3$), Aluminum oxide, Glass-Ceramic, including Bioglass(Ceravital), Carbons, including allotropic, crystalline, diamond, and graphite, quasi-crystalline glassy carbon, and/or pyrolytic carbon.

In vitro Skin Flux Using Human Cadaver Skin and Erythropoietin as Model Drug

In order to measure in vitro transdermal flux amount, a Franz cell was modified to have a volume of 6.9 ml. Full thickness (about 3 mm) human cadaver skin (The New York Firefighter Skin Bank, New York, N.Y. 10021) was used and an exemplary configuration for this test is depicted in FIG. 5A in which skin 510 is mounted on Franz cell 520. The micro-perforator array 530 (with occlusive layer; not shown) is inserted into the skin 510 using applicator 540 or manually. The micro-perforators were formulated with fast dissolving gel (e.g., dextran) and 130 microgram of erythropoietin, using a dissolution-dry method. The drug micro-perforators were then manually inserted on top of the cadaver skin and the skin sample with the micro-perforators inserted were placed on the Franz cell covered with a plastic occlusion film. The occlusion film was of advantageous since the film created a high humid environment and promoted dissolution of the micro-perforators. The receiver was maintained at human skin temperature (about 32° C.) during the 48 hour experiment and the fluid in the receiver was stirred at 400 rpm. At predetermined times (3, 6, 9, 12, 24, 36, and 48 hours), samples were collected and assayed for drug content by HPLC. The cumulated diffused amount and flux profile was plotted over time, and the results are depicted in FIG. 5B.

In Vitro Glucose Colorimetric Monitoring Using Human Cadaver Skin

The following example is based on a method of glucose monitoring using a micro-perforator patch with a fluorescence sensor layer. A gel comprising Concanavalin A and fluorescein dextran is used for fabricating the micro-perforator and a gel layer laminated over the micro-perforator layer. Once the micro-channel is created, glucose in interstitial fluid can reacted with the sensor needle and/or sensor layer: Concanavalin A binds competitively with fluorescein dextran and interstitial glucose. As the glucose concentration increases, fluorescein is displaced from the dextran and thus fluorescence increases proportional to the glucose concentration. Fluorescence from fluorescein can be measured by a fluorescence reader that is optically coupled to the sensor needle and/or sensor layer.

To measure in vitro glucose, a Franz cell was modified to 6.9 ml, and full thickness (about 3 mm) human cadaver skin was used. The micro-perforator was formulated with fast dissolving gel and formulation was prepared by dissolution-dry method. The micro-perforators were manually inserted into the cadaver skin, and a commercially available glucose sensor (LifeScan One-Touch profile) was placed on top of the inserted micro-perforators 5 minutes. The bottom chamber of the Franz cell was filled with glucose solutions with glucose concentrations between 0-500 mg/dl, and the temperature was maintained at 32° C. during the entire experiment. The receiver solution was stirred at 400 rpm. Results are listed in the table of FIG. 6. As expected, there is a reasonable correlation between the glucose concentration between bottom chamber (the glucose donor) and the micro-channels in the skin that were created by inserting the micro-perforators.

Figure 7A:
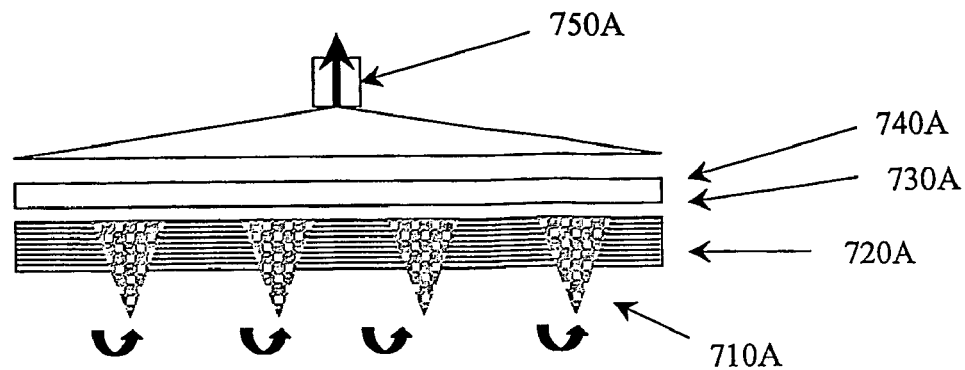
FIG. 7A is a schematic representation of continuous glucose monitoring.

Of course, it should be recognized that glucose monitoring may be performed continuously or intermittently, and an exemplary modes of continuous glucose monitoring is depicted in FIG. 7A where interstitial fluid (movement indicated by arrows) is transported via a plurality of porous micro-perforators (or channels created by same) 710A through the stratum corneum 720A. The glucose then contacts the enzyme layer (e.g., using glucose oxidase) 730A, which provides a redox reaction that is detected/picked up in the electrochemical sensor layer 740A. A vacuum source 750A (manual or automatic) will provide movement of the interstitial fluid.

Figure 7B:
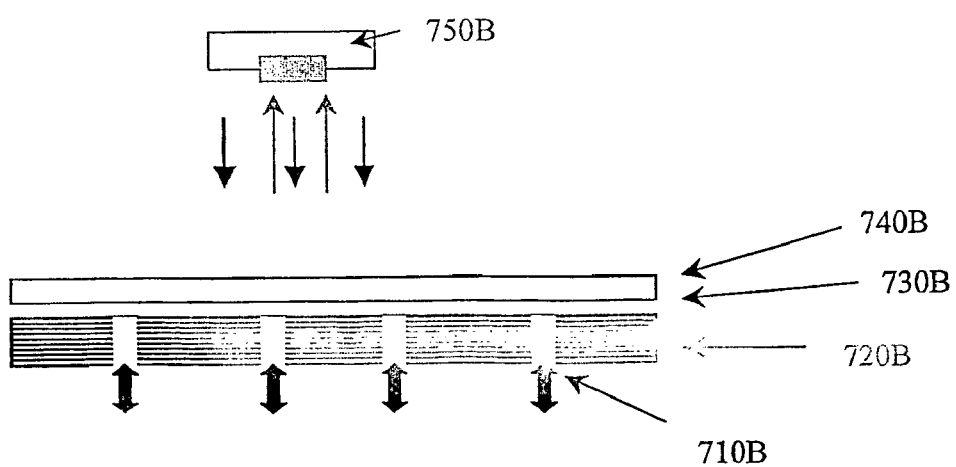
FIG. 7B is a schematic representation of intermittent glucose monitoring.

Similarly, intermittent glucose monitoring may be performed as depicted in FIG. 7B where interstitial fluid (movement indicated by arrows) is transported via a plurality of porous micro-perforators (or channels created by same) 710B through the stratum corneum 720A. The glucose then contacts an optional enzyme layer 730B and detection layer 740A, in which a change of glucose will change an optically detectable parameter (e.g., fluorescence). An optical detector 750B will then detect a signal change, which is correlated with a glucose concentration.

Consequently, the inventors contemplate that suitable method of manufacture of a micro-perforator may include one step in which a solidifiable material is provided and formed into a desired micro-perforator shape, optionally in admixture with a diagnostic or therapeutic agent. The step of forming the solidifiable material preferably includes a step of solidifying the solidifiable material such that the solidified material in the desired micro-perforator shape has a plurality of pores that optionally comprise the diagnostic or therapeutic agent. The solidified material in the desired micro-perforator shape may then be contacted with the diagnostic or therapeutic agent such that the diagnostic or therapeutic agent is at least partially enclosed in the plurality of pores.

As already discussed above, especially suitable solidifiable materials include sol/gel materials, sinterable materials, gelling agents and/or a viscous materials (optionally comprising a therapeutic and/or diagnostic agent), and it is further preferred that the material is forced into a mold using positive pressure (e.g., via centrifugation, or air pressure into the mold) and/or negative pressure (e.g., vacuum applied through a porous mold portion).

In still further preferred aspects of the inventive subject matter, the step of forming the solidifiable material includes a step in which the material is dried or sintered such that the formed and dried/sintered solidifiable material will be shrunk. Such shrinking may advantageously facilitate removal of the formed micro-perforator from the mold as well as decrease the apex angle of the micro-perforator. Depending on the material employed for the manufacture of contemplated micro-perforator, it should be appreciated that such perforators and devices may dissolve in the skin over a predetermined period of time. Additionally, multiple layers may be included in suitable micro-perforators wherein each layer may include the same or a different therapeutic and/or diagnostic agent.

Therefore, suitable micro-perforators will include those comprising a porous material and optionally comprising at least one of a diagnostic and/or therapeutic agent, wherein the micro-perforator is substantially insoluble (or dissoluble in a skin of a person when applied to the skin over a predetermined period greater than one hour, but less than a day) in a skin of a person when applied to the skin. It is further contemplated that the diagnostic and/or therapeutic agent may be included in the void volume of the pores, but may also be at least in part provided by a reservoir fluidly coupled to the micro-perforators (and optionally actuated by a pump).

Where the micro-perforators are dissoluble, it is particularly preferred that the device comprises a plurality of dissolvable micro-perforators in a predetermined array, wherein at least some of the micro-perforators are coupled to an occlusive backing that enhances dissolution of the micro-perforators.

In yet another aspect of the inventive subject matter, a diagnostic device may include a porous micro-perforator that comprises at least one of an analyte compartment and a reagent compartment, wherein the at least one of the analyte compartment and reagent compartment is fluidly coupled to a body fluid of a person when the micro-perforator is inserted into a skin of the person, and wherein the at least one of the analyte compartment and reagent compartment is operationally coupled to a detector. Where the porous micro-perforator dissolves, it is contemplated that a conduit between the body fluid and the detector is formed by dissolution of the porous micro-perforator.

Thus, specific embodiments and applications of solid micro-perforators and methods of use have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of manufacture of a micro-perforator, comprising:
   providing a solidifiable material, and forming the solidifiable material, optionally in admixture with a diagnostic or therapeutic agent into a desired micro-perforator shape;
   wherein the step of forming the solidifiable material includes a step of solidifying the solidifiable material such that the solidified material in the desired micro-perforator shape has a plurality of pores that optionally comprise the diagnostic or therapeutic agent; and
   optically contacting the solidified material in the desired micro-perforator shape with the diagnostic or therapeutic agent such that the diagnostic or therapeutic agent is at least partially enclosed in the plurality of pores,
   wherein the solidifiable material shrinks during the step of solidifying the solidifiable material, and
   wherein shrinking of the solidifiable material is controlled by one of formulation of the solidifiable material and drying the solidifiable material to reduce an apex angle of the micro-perforator.

2. The method of claim 1 wherein the solidifiable material comprises a sol/gel material.

3. The method of claim 2 wherein the sol/gel material further comprises the diagnostic or therapeutic agent.

4. The method of claim 3 wherein the step of forming comprises a step of filing the sol/gel material into a mold to which a force is applied to improve settling of the sol/gel material into the mold, and wherein the step of forming is performed at ambient temperature.

5. The method of claim 2 wherein porosity of the solidified sol/gel material is controlled via adjustment of the pH in the unsolidified sol/gel material.

6. The method of claim 1 wherein the solidifiable material comprises a sinterable material.

7. The method of claim 6 wherein the sinterable material further comprises the diagnostic or therapeutic agent.

8. The method of claim 6 wherein porosity of the solidified sinterable material is controlled via at least one of pressure, particle size and temperature during the step forming the solidifiable material.

9. The method of claim 1 wherein the solidifiable material comprises a gelling agent or a viscous material, and wherein the step of forming the solidifiable material includes a step of removing air bubbles from the gelling agent or viscous material using positive or negative pressure.

10. The method of claim 1 wherein the solidified material in the desired micro-perforator shape that optionally comprises the diagnostic or therapeutic agent dissolves in a skin of a person over a predetermined period when applied to the skin.

11. The method of claim 10 wherein dissolution of the micro-perforator is completed in less than one day.

12. The method of claim 1 further comprising a step in which the solidified material is the desired micro-perforator shape is contacted with a second solidifiable material, and in which the second solidifiable material is formed into a desired micro-perforator shape to provide a laminated micro-perforator.

* * * * *